US010206711B1

(12) United States Patent
Jadhav et al.

(10) Patent No.: US 10,206,711 B1
(45) Date of Patent: Feb. 19, 2019

(54) SURGICAL INSTRUMENTS FOR ENGAGING TISSUE TO STABILIZE TISSUE AND FACILITATE TISSUE MANIPULATION

(71) Applicant: COVIDIEN LP, Mansfield, MA (US)

(72) Inventors: Amarsinh D. Jadhav, Karnataka (IN); Rajat R. Rokde, Pune (IN); Yogesh K. Vikharankar, Nashik (IN)

(73) Assignee: COVIDIEN LP, Mansfield, MA (US)

( * ) Notice: Subject to any disclaimer, the term of this patent is extended or adjusted under 35 U.S.C. 154(b) by 7 days.

(21) Appl. No.: 15/666,784

(22) Filed: Aug. 2, 2017

(51) Int. Cl.
*A61B 17/42* (2006.01)
*A61B 1/00* (2006.01)
*A61B 17/34* (2006.01)
*A61B 17/29* (2006.01)
*A61B 17/02* (2006.01)

(52) U.S. Cl.
CPC ...... *A61B 17/4241* (2013.01); *A61B 1/00066* (2013.01); *A61B 17/3417* (2013.01); *A61B 17/0206* (2013.01); *A61B 2017/2901* (2013.01)

(58) Field of Classification Search
CPC ............ A61B 17/4241; A61B 1/00066; A61B 17/3417
See application file for complete search history.

(56) References Cited

U.S. PATENT DOCUMENTS

| 5,520,634 | A | 5/1996 | Fox et al. |
| 6,039,748 | A | 3/2000 | Savage et al. |
| 6,165,188 | A | 12/2000 | Saadat et al. |
| 6,468,228 | B1 | 10/2002 | Topel et al. |
| 6,677,393 | B1* | 1/2004 | Zech ........................ A61K 6/10 |
| | | | 524/366 |
| 6,681,946 | B1* | 1/2004 | Jansen .................. A61J 1/1406 |
| | | | 141/329 |
| 6,821,285 | B2 | 11/2004 | Laufer et al. |
| 7,033,357 | B2 | 4/2006 | Baxter et al. |
| 7,918,795 | B2 | 4/2011 | Grossman |
| 8,308,746 | B2 | 11/2012 | Pravong et al. |
| 8,685,031 | B2* | 4/2014 | Kleiner ................... A61F 2/447 |
| | | | 606/92 |
| 9,668,763 | B2 | 6/2017 | Sartor et al. |
| 2004/0071786 | A1* | 4/2004 | Grippi ................... A61L 24/106 |
| | | | 424/530 |

(Continued)

FOREIGN PATENT DOCUMENTS

WO   2009/039506 A1   3/2009

*Primary Examiner* — Christian Sevilla

(57) ABSTRACT

A surgical instrument includes a stationary shaft defining a conduit and a movable shaft slidably disposed therein. A surgical tool extends distally from the movable shaft and a cup extends distally from the stationary shaft. The cup includes a body defining one or more channels, an annular rim disposed at the distal end portion thereof and defining a plurality of apertures each in fluid communication with one of the channels, and a cap disposed at the proximal end portion of the body and defining a lumen fluidly coupling the one or more channels with the conduit. A central aperture of the cap slidably receives the surgical tool and/or the movable shaft as the movable shaft slides from a retracted position, wherein the surgical tool is disposed proximally of the distal end portion of the cup, and an extended position, wherein the surgical tool extends through and distally from the cup.

15 Claims, 6 Drawing Sheets

(56) References Cited

U.S. PATENT DOCUMENTS

| | | |
|---|---|---|
| 2005/0288622 A1* | 12/2005 | Albrecht ............ A61B 17/3417 |
| | | 604/23 |
| 2007/0225745 A1 | 9/2007 | Amal et al. |
| 2008/0039883 A1 | 2/2008 | Nohilly |
| 2008/0269772 A1 | 10/2008 | Choi |
| 2011/0121049 A1 | 5/2011 | Malinouskas et al. |
| 2012/0316572 A1 | 12/2012 | Rosenblatt et al. |
| 2013/0123797 A1 | 5/2013 | Livneh |
| 2014/0257112 A1 | 9/2014 | Siegel |
| 2015/0011942 A1* | 1/2015 | Ito .................... A61M 25/0631 |
| | | 604/165.02 |
| 2016/0235440 A1* | 8/2016 | Goldberg ........... A61B 17/0401 |

* cited by examiner

SURGICAL INSTRUMENTS FOR ENGAGING TISSUE TO STABILIZE TISSUE AND FACILITATE TISSUE MANIPULATION

TECHNICAL FIELD

The present disclosure generally relates to surgical instruments, and more particularly, to surgical instruments for engaging tissue, such as, for example, uterine tissue, to stabilize tissue and facilitate manipulation of the tissue.

BACKGROUND

Certain surgical procedures are performed to remove uterine tissue, such as hysterectomies, fibroidectomies, myomectomies, and the like. One or more of these procedures can be performed laparoscopically by passing surgical instrument(s) down a cannula so that a distal working end of the surgical instrument(s) can be positioned within an internal surgical site, while operated from a proximal manipulator of the surgical instrument(s). In these instances, a surgical instrument inserted through an abdominal cannula may be utilized to engage a uterus, uterine fibroids (known as leiomyomas), or other tissue to enable manipulation of the tissue relative to a moving cutting tool, such as a morcellator, operating within the internal surgical site.

To stabilize the uterus or other tissue during a procedure, for example, the clinician may employ mechanical graspers or a screw. However, due to the slippery nature of uterine tissue and its size and bulky shape, the clinician may be required to make several attempts to reposition the mechanical graspers and/or screw in order to secure the uterus or other tissue in position. Thus, although mechanical graspers and screws are effective, they may be improved.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

A surgical instrument provided in accordance with aspects of the present disclosure includes a shaft assembly, a surgical tool, and a cup. The shaft assembly includes a stationary shaft and a movable shaft slidably disposed within the stationary shaft. The stationary shaft defines a conduit extending therethrough. The surgical tool extends distally from a distal end portion of the movable shaft. The cup extends distally from a distal end portion of the stationary shaft. The cup includes a body, an annular rim, and a cap. The body includes a proximal end portion and a distal end portion and defines one or more channels extending from the proximal end portion to the distal end portion thereof. The annular rim is disposed at the distal end portion of the body and defines a plurality of apertures therethrough, each of which is disposed in fluid communication with one of the channels. The cap is disposed at the proximal end portion of the body and defines a lumen fluidly coupling the channels with the conduit and a central aperture configured to slidably receive the surgical tool and/or the movable shaft. The movable shaft is slidable relative to the stationary shaft from a retracted position, wherein the surgical tool is disposed proximally of the distal end portion of the cup, and an extended position, wherein the surgical tool extends through and distally from the cup.

In an aspect of the present disclosure, the surgical tool is a tissue-engaging implement. The tissue-engaging implement may be a screw and, more specifically, may be a screw defining a corkscrew-shaped configuration.

In another aspect of the present disclosure, the plurality of apertures is equally-spaced about a circumference of the annular rim of the cup.

In still another aspect of the present disclosure, a compliant annular ring is disposed about the annular rim of the cup. In such aspects, the plurality of apertures extends through the compliant annular rim.

In yet another aspect of the present disclosure, the movable shaft is rotatable relative to the stationary shaft to rotate the surgical tool relative to the cup.

In still yet another aspect of the present disclosure, the stationary shaft defines an inlet opening at a proximal end portion thereof. The inlet opening is disposed in fluid communication with the conduit and adapted to connect to a pump.

A surgical system provided in accordance with aspects of the present disclosure includes a pump and a surgical instrument. The surgical instrument includes a shaft assembly, a surgical tool, and a cup. The shaft assembly includes a stationary shaft and a movable shaft slidably disposed within the stationary shaft. The stationary shaft defines a conduit extending therethrough having a proximal end portion fluidly coupled to the pump. The surgical tool extends distally from a distal end portion of the movable shaft. The cup extends distally from a distal end portion of the stationary shaft. The cup includes a body, an annular rim, and a cap. The body includes a proximal end portion and a distal end portion and defines one or more channels extending from the proximal end portion to the distal end portion thereof. The annular rim is disposed at the distal end portion of the body and defines a plurality of apertures therethrough, each of which is disposed in fluid communication with one of the channels. The cap is disposed at the proximal end portion of the body and defines a lumen fluidly coupling the channels with the conduit and a central aperture configured to slidably receive the surgical tool and/or the movable shaft. Upon activation of the pump, suction is established through the conduit, the lumen, the one or more channels, and the apertures.

In an aspect of the present disclosure, the movable shaft is slidable relative to the stationary shaft from a retracted position, wherein the surgical tool is disposed proximally of the distal end portion of the cup, and an extended position, wherein the surgical tool extends through and distally from the cup.

In another aspect of the present disclosure, the surgical tool is a tissue-engaging implement. The tissue-engaging implement may be a screw and, more specifically, may be a screw defining a corkscrew-shaped configuration.

In yet another aspect of the present disclosure, the system further includes a connector fluidly coupling the pump with the proximal end portion of the conduit.

In still another aspect of the present disclosure, a compliant annular ring is disposed about the annular rim of the cup including the plurality of apertures extending therethrough.

In still yet another aspect of the present disclosure, the movable shaft is rotatable relative to the stationary shaft to rotate the surgical tool relative to the cup.

A method provided in accordance with aspects of the present disclosure includes positioning a cup against a target area of the tissue, applying suction to the cup to suction the target area of tissue against the cup, thereby stabilizing the target area of tissue, and advancing a surgical tool through an interior of the cup and into engagement with the target area of tissue.

In an aspect of the present disclosure, the surgical tool is advanced and rotated into engagement with the target area of tissue.

In another aspect of the present disclosure, the method further includes maneuvering the surgical tool to manipulate the target area of tissue.

In another aspect of the present disclosure, the method further includes cutting the target area of tissue.

BRIEF DESCRIPTION OF THE DRAWINGS

The above and other aspects and features of the present disclosure will become more apparent in light of the following detailed description when taken in conjunction with the accompanying drawings, in which.

DETAILED DESCRIPTION

Figure 1:
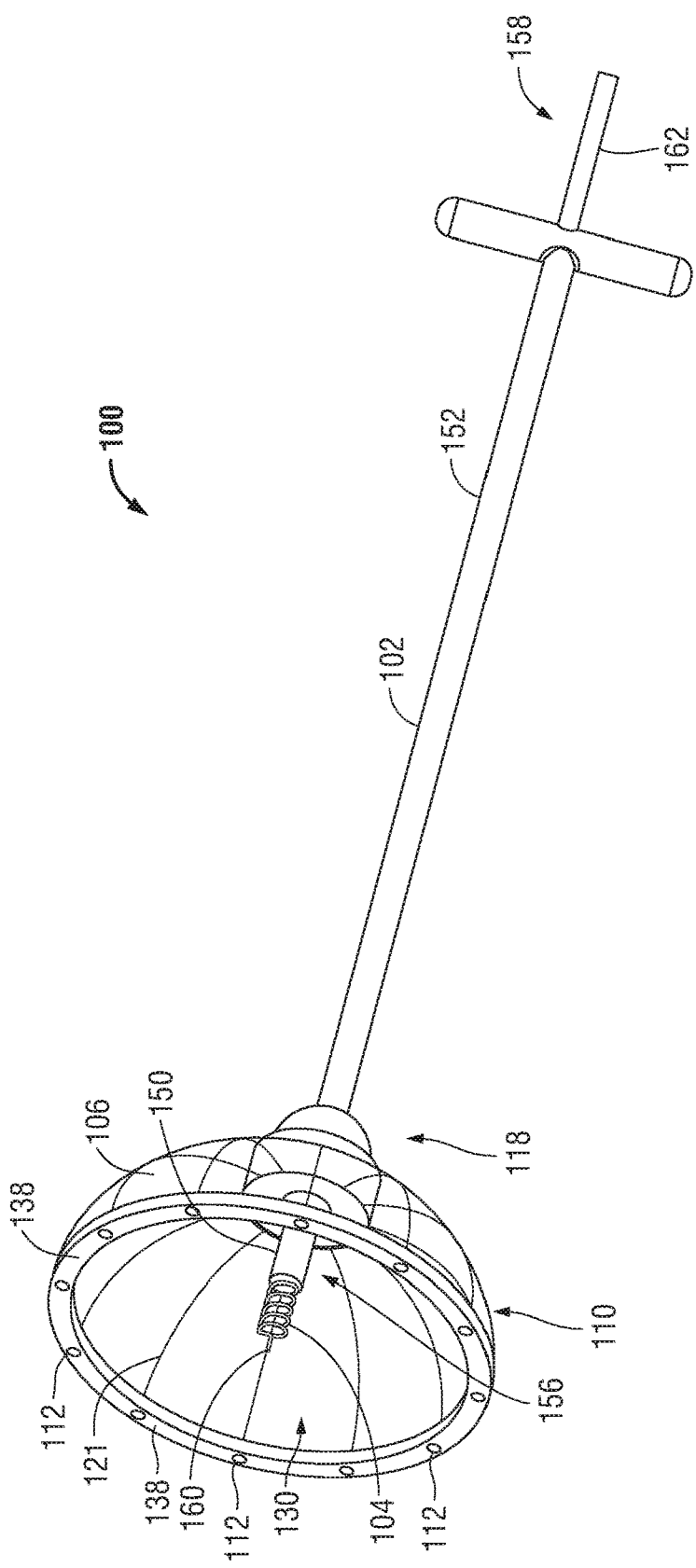
FIG. 1 is a front, perspective view of a surgical instrument provided in accordance with aspects of the present disclosure.
Figure 2:
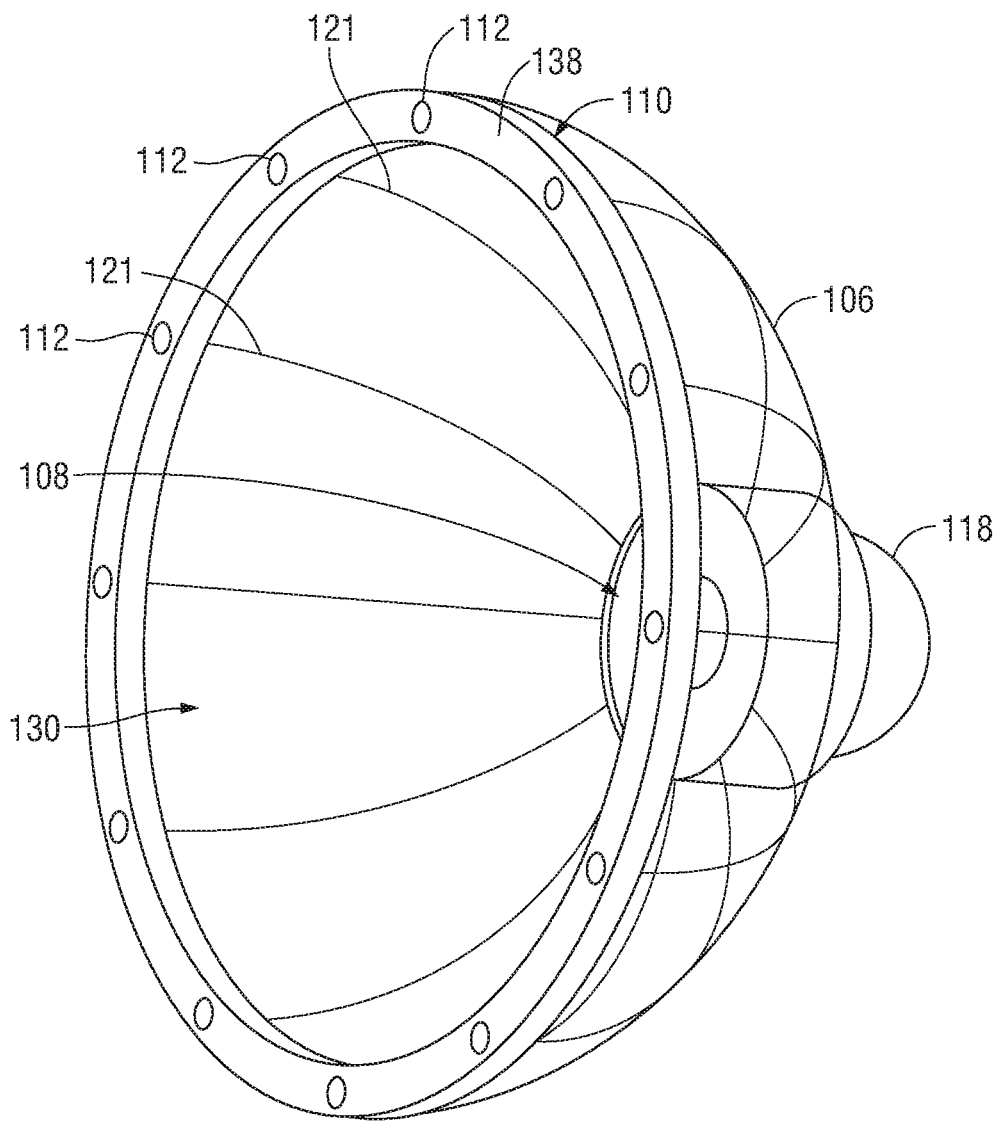
FIG. 2 is an enlarged, front, perspective view of a cup of the surgical instrument of FIG. 1.
Figure 3:
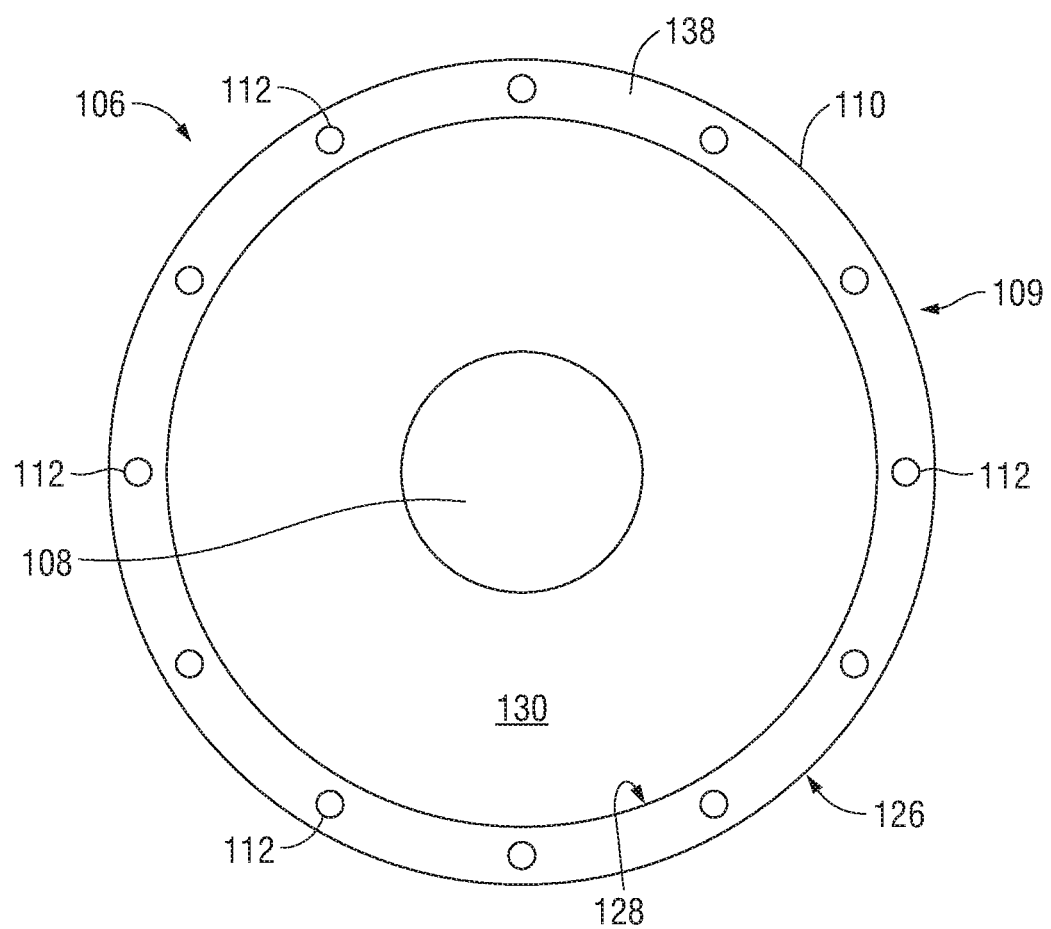
FIG. 3 is an end view of the cup of FIG. 2 with the annular ring removed therefrom.

Surgical instruments configured to engage tissue to stabilize tissue and facilitate manipulation of tissue are provided, each generally including a shaft assembly having a movable member with a distal end portion including a screw extending distally therefrom and a stationary member defining a vacuum conduit, and a cup having a cap through which the movable member is slidably disposed and to which the stationary member is coupled. A vacuum pump may be coupled to the stationary member to provide suction to the cup via the vacuum conduit. In use, the surgical instrument is maneuvered such that the cup is disposed about a target area of tissue. The vacuum pump is then turned on to suction the target area to the cup, thereby stabilizing the target area to enable advancement of the movable member distally towards the target area to engage the target area with the screw. In embodiments, the movable member may be simultaneously advanced and rotate to thereby rotate the screw into engagement with the target area. Fluid, debris, and/or other biological matter may be collected within the cup and carried away via the suction. These and other aspects and features of the present disclosure are detailed below.

With reference now to FIGS. 1-4, a surgical instrument provided in accordance with the present disclosure and configured to engage tissue to stabilize tissue and facilitate manipulation of tissue is shown generally identified by reference numeral 100. Surgical instrument 100 includes a shaft assembly 102, a screw 104 extending distally from the shaft assembly 102, and a cup 106 having a central opening 108 through which the shaft assembly 102 extends. To permit the cup 106 to be suctioned against a surface of tissue, a rim portion 110 of the cup 106 includes one or more suction holes 112 communicating with radial apertures 116 in a cap 118 covering the central opening 108 of the cup 106 and the radial apertures 116 communicate, via channel(s) 121 and annular lumen 142, with a vacuum lumen 120 that extends through at least a portion of the shaft assembly 102 to a proximal end portion 122 of shaft assembly 102 that is configured to couple to a vacuum pump 114 via a pump connection 180 (see FIG. 4).

The cup 106 is generally dome-shaped with the central opening 108 formed in the apex of the dome. In embodiments, the cup 106 is made of a durable, biocompatible plastic or polymer and may be transparent or semi-transparent. Other suitable materials configured to maintain structural integrity the cup 106 when pressurized are also contemplated.

The cup 106 is made up of a body 109 having an outer surface 126 and an inner surface 128 that defines an interior cavity 130. The body 109 includes one or more channels 121 formed between the outer and inner surfaces 126, 128, which extend from the rim portion 110 of the cup 106 to the central opening 108 of the cup 106. The one or more channels 121 terminate at the rim portion 110 at corresponding suction holes 112. Although the outer and inner surfaces 126, 128 are illustrated as being smooth such that the presence of the channel(s) 121 is not immediately visibly detectable, it will be appreciated that the outer surface 126 and/or inner surface 128 of the cup 106 may alternatively include ridges beneath which the channel(s) 121 are located. Further, although suction holes 112 are illustrated as generally circular, other suitable configurations, e.g., slotted, elongated, rectangular, etc., are also contemplated. Additionally, although distinct channels 121 are illustrated, it is also contemplated that one or more channels 121 be formed via a hollow or partially hollow (with or without partitions) body 109 of the cup 106.

In embodiments, an annular ring 138 is disposed over the rim portion 110 of the cup 106 to cover the distally-facing surface and inner and outer edges of the rim portion 110 of the cup 106. The annular ring 138 may define apertures that communicate with apertures or other openings defined within the rim portion 110 to define suction holes 112 therethrough. The annular ring 138 may be formed of a compliant material, such as rubber, a foam, a polymeric material, or the like, and may be adhered with an adhesive or molded over the rim portion 110 of the cup 106.

Continuing with reference to FIGS. 1-4, as noted above, the plurality of channels 121 extending through the body 109 of the cup 106 terminate at the central opening 108. The cap 118 is disposed about the outer surface 126 of the cup 106 at the apex thereof and, more particularly, over the central opening 108. The cap 118 defines radial apertures 116 that align with corresponding outlets of the one or more channels 121. The radial apertures 116 provide communication with an annular lumen 142 formed in the cap 118, and the annular lumen 142 communicates with the vacuum lumen 120 that extends through at least a portion of the shaft assembly 102, as described in detail below. The cap 118 further includes a central aperture 144 within which a portion of the shaft assembly 102 is slidably disposed. Although not specifically depicted, in other embodiments, the cap 118 is disposed on the inner surface 128 of the cup 106 within the interior cavity 130 defined by the body 109 of the cup 106.

The shaft assembly 102 includes a movable member 150 and a stationary member 152. The movable member 150 extends through a main lumen 154 formed through the stationary member 152 and has a length that is greater than that of the stationary member 152. In particular, the movable member 150 is configured to have a middle portion that is the length of the stationary member, a distal end portion 156 that extends distally from the stationary member 152 and through the central opening 108 of the cup 106 at least partially through the interior cavity 130 of the cup 106, and a proximal end portion 158 that extends from the stationary member 152 in a proximal direction a length that is sufficient to enable manipulation of the movable member 150 relative to the stationary member 152 to advance the distal end portion 156 of the movable member 150 into tissue a desired distance.

In embodiments, the distal end portion 156 of the movable member 150 includes the screw 104. The screw 104 is made of stainless steel or another biocompatible material capable of maintaining structural integrity when inserted into tissue and is spiral or corkscrew shaped. The screw is engaged to the distal end portion 156 of the movable member 150 and extends distally therefrom. The screw 104 has a tip 160 that is sharp in order to more easily puncture tissue when the screw 104 is rotated in a particular direction. In other embodiments, the tip 160 is blunt.

The proximal end portion 158 of the movable member 150 extends proximally out of the main lumen 154 of the stationary member 152, as noted above, so as to provide a handle portion 162 for manipulation, e.g., translation and/or rotation, by a user. The handle portion 162 may include a textured surface, knob, or other mechanical feature to improve the user's grasp of the movable member 150. In embodiments, the movable member 150 slidably contacts the interior surface of the stationary member 152 that defines the main lumen 154. In other embodiments, a small annular gap is maintained between the movable member 150 and the surface of the stationary member 152 in any suitable fashion, e.g., via washers, bearings, etc.

Figure 4:
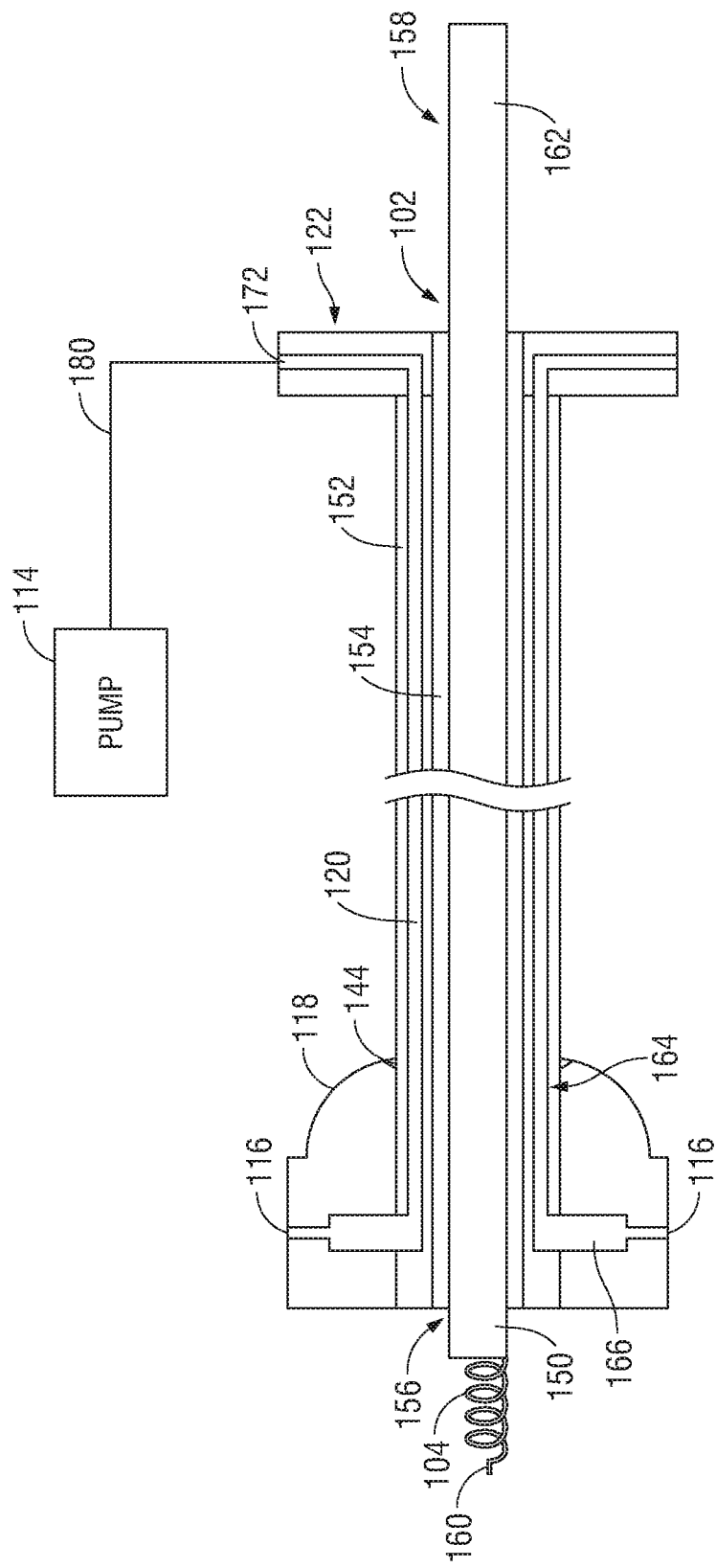
FIG. 4 is a longitudinal, cross-sectional view of the surgical instrument of FIG. 1, shown operably coupled to a pump.
Figure 5:
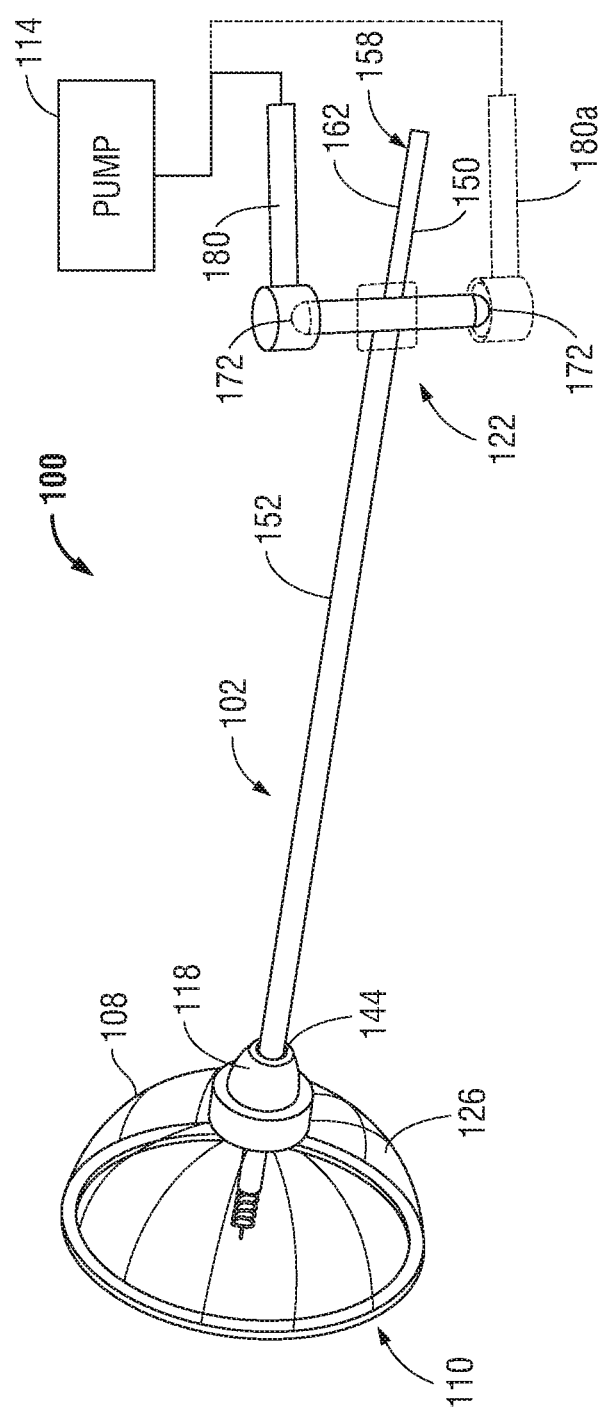
FIG. 5 is a rear, perspective view of the surgical instrument of FIG. 1, shown operably coupled to a pump.

The stationary member 152 is configured to maintain its stiffness throughout the entirety of a surgical procedure. As illustrated in FIG. 4, a distal end portion 164 of the stationary member 152 extends through the central aperture 144 of the cap 118. The stationary member 152 may be either temporarily or permanently coupled to the cap 118. An annular opening 166 is formed in the distal end portion 164 of the stationary member 152 and is aligned with the annular lumen 142 of the cap 118. In other embodiments, a plurality of annular openings is included in the distal end portion 164, each annular opening being aligned with the annular lumen 142. The vacuum lumen 120 extends from the radial annular opening 166 to one or more vacuum pump inlet openings 172 formed at the proximal end portion 122 of the stationary member 152. In embodiments, with additional reference to FIG. 5, a pump connection 180 is coupled to the one or more inlet openings 172. In other embodiment, two pump connections 180, 180a (shown in phantom) are coupled to corresponding ones of the inlet openings 172.

Figure 6:
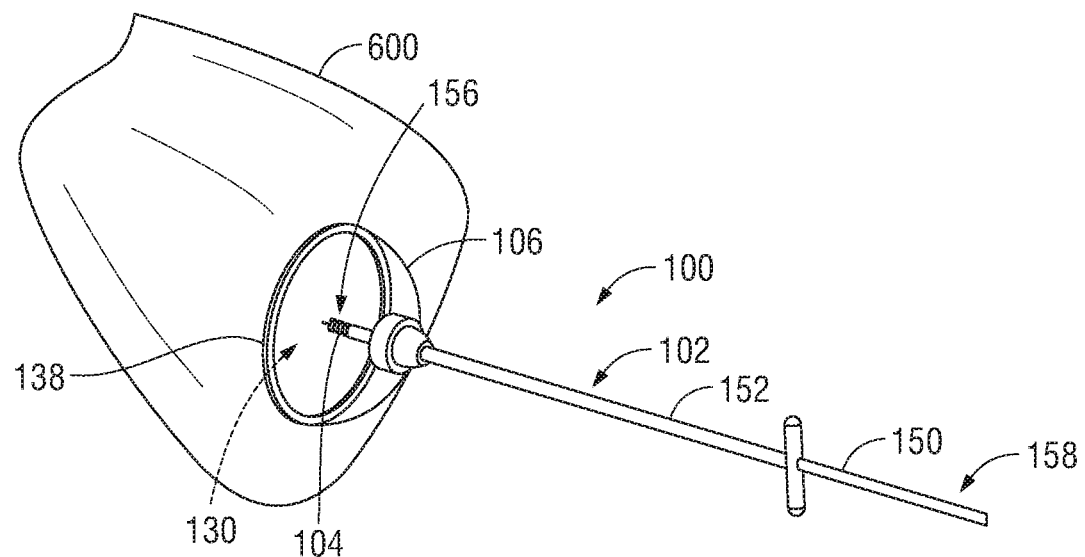
FIGS. 6 and 7 are perspective views of the surgical instrument of FIG. 1 in use engaging tissue to stabilize tissue and facilitate manipulation of tissue.
Figure 7:
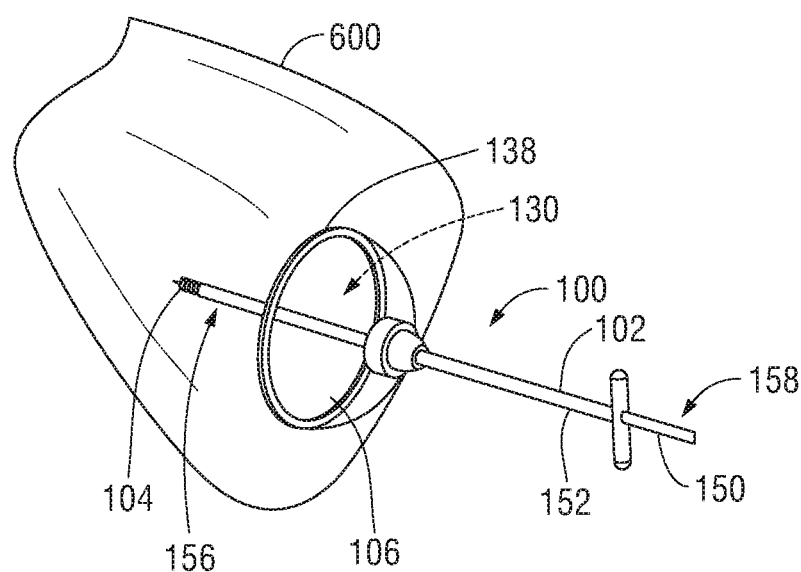

With reference to FIGS. 6 and 7, in conjunction with FIGS. 1-4, during a surgical procedure, the surgical instrument 100 is navigated to a target area of tissue with the movable member 150 of the shaft assembly 102 disposed in a retracted position, wherein the screw 104 is disposed within the main lumen 154 of the stationary member 152 or protruding minimally therefrom into (but not beyond) the internal cavity 130 of the cup 106.

Once disposed in a desired position, the annular ring 138 disposed on the rim portion 110 of the cup 106 is urged against the surface of the target area of tissue 600, and the vacuum pump 114 is activated to a powered on condition. As a result, suction is created through the vacuum lumen 120 of the stationary member 152 of the shaft assembly 104, the annular lumen 142 of the cap 118, the channels 121 of the cup 106, and the suction holes 112 defined through rim portion 110 of the cup 106 and the annular ring 138 to cause the cup 106 to be suctioned to the target area of tissue 600. In this manner, the cup 106 stabilizes the target area of tissue 600.

With the surgical instrument 100 suctioned to the target area of tissue 600, the proximal end portion 158 of the movable member 150 is urged distally relative to the stationary member 152 to advance the distal end portion 156 of the movable member 150 and, thus, screw 104 into the target area of tissue 600. In embodiments, the proximal end portion 158 of the movable member 150 is rotated relative to the stationary member 152 in a direction corresponding to the corkscrew shape of the screw 104 during the distal advancement of the movable member 150 to permit the screw 104 to engage and embed within the target area of tissue 600. By using the suction provided by cup 106, engagement of the screw 104 within the target area of tissue 600 is more easily, accurately, and securely achieved.

The suction provided by cup 106 also enables fluid, debris, and/or other biological matter to be suctioned into the cup 106 and carried away via the suction path detailed above. This may be accomplished before suctioning the cup 106 to the target area of tissue 600, after suctioning the cup 106 to the target area of tissue 600, and/or while the cup 106 is suctioned to the target area of tissue 600. Additional apertures communicated with the suction path may be provided on the interior surface 128 of the body 109 of the cup 106, the exterior surface 126 of the body 109 of the cup 106, and/or on another portion of the cup 106 for these purposes.

Once screw 104 is engaged within the target area of tissue 600, shaft assembly 102 may be maneuvered to manipulate the target area of tissue 600 to a desired orientation and/or position such as, for example, to facilitate cutting, e.g., morcellating, the target area of tissue 600. Alternatively, stationary member 152 and cup 106 may be withdrawn proximally about movable member 150 such that movable member 150 may be maneuvered to manipulate the target area of tissue 600 to a desired orientation and/or position.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A surgical instrument, comprising:
   a shaft assembly including a stationary shaft and a movable shaft slidably disposed within the stationary shaft, the stationary shaft defining a conduit extending therethrough;
   a surgical tool extending distally from a distal end portion of the movable shaft;
   a cup extending distally from a distal end portion of the stationary shaft, the cup including:
      a body including a proximal end portion and a distal end portion, the body defining one or more channels extending from the proximal end portion to the distal end portion thereof;
      an annular rim disposed at the distal end portion of the body, the annular rim defining a plurality of apertures therethrough, each aperture disposed in fluid communication with one of the one or more channels; and
      a cap disposed at the proximal end portion of the body, the cap defining a lumen fluidly coupling the one or more channels with the conduit, the cap defining a central aperture configured to slidably receive at least one of the surgical tool or the movable shaft therethrough,
   wherein the movable shaft is slidable relative to the stationary shaft from a retracted position, wherein the surgical tool is disposed proximally of the distal end portion of the cup, and an extended position, wherein the surgical tool extends through and distally from the cup.

2. The surgical instrument of claim 1, wherein the surgical tool is a tissue-engaging implement.

3. The surgical instrument of claim 2, wherein the tissue-engaging implement is a screw.

4. The surgical instrument of claim 3, wherein the screw defines a corkscrew-shaped configuration.

5. The surgical instrument of claim 1, wherein the plurality of apertures is equally-spaced about a circumference of the annular rim of the cup.

6. The surgical instrument of claim 1, further including a compliant annular ring disposed about the annular rim of the cup, wherein the plurality of apertures extends through the compliant annular rim.

7. The surgical instrument of claim 1, wherein the movable shaft is rotatable relative to the stationary shaft to rotate the surgical tool relative to the cup.

8. The surgical instrument of claim 1, wherein the stationary shaft defines an inlet opening at a proximal end portion thereof, the inlet opening disposed in fluid communication with the conduit and adapted to connect to a pump.

9. A surgical system, comprising:
   a pump; and
   a surgical instrument, including:
      a shaft assembly including a stationary shaft and a movable shaft slidably disposed within the stationary shaft, the stationary shaft defining a conduit extending therethrough, a proximal end portion of the conduit fluidly coupled to the pump;
      a surgical tool extending distally from a distal end portion of the movable shaft;
      a cup extending distally from a distal end portion of the stationary shaft, the cup including:
         a body including a proximal end portion and a distal end portion, the body defining one or more channels extending from the proximal end portion to the distal end portion thereof;
         an annular rim disposed at the distal end portion of the body, the annular rim defining a plurality of apertures therethrough, each aperture disposed in fluid communication with one of the one or more channels; and
         a cap disposed at the proximal end portion of the body, the cap defining a lumen fluidly coupling the one or more channels with the conduit, the cap defining a central aperture configured to slidably receive at least one of the surgical tool or the movable shaft therethrough,
      wherein, upon activation of the pump, suction is established through the conduit, the lumen, the one or more channels, and the apertures.

10. The system of claim 9, wherein the movable shaft is slidable relative to the stationary shaft from a retracted position, wherein the surgical tool is disposed proximally of the distal end portion of the cup, and an extended position, wherein the surgical tool extends through and distally from the cup.

11. The system of claim 9, wherein the surgical tool is a tissue-engaging implement.

12. The system of claim 11, wherein the tissue-engaging implement is a screw defining a corkscrew-shaped configuration.

13. The system of claim 9, further comprising a connector fluidly coupling the pump with the proximal end portion of the conduit.

14. The system of claim 9, further including a compliant annular ring disposed about the annular rim of the cup, wherein the plurality of apertures extends through the compliant annular rim.

15. The system of claim 9, wherein the movable shaft is rotatable relative to the stationary shaft to rotate the surgical tool relative to the cup.

* * * * *